United States Patent [19]

Fratesi

[11] Patent Number: 5,005,565
[45] Date of Patent: Apr. 9, 1991

[54] THIGH AND KNEE PROTECTIVE DEVICE

[76] Inventor: Gary R. Fratesi, 112-C Heritage Village, Southbury, Conn. 06418

[21] Appl. No.: 392,426

[22] Filed: Aug. 10, 1989

Related U.S. Application Data

[63] Continuation-in-part of Ser. No. 203,092, Jun. 7, 1988, abandoned.

[51] Int. Cl.$^5$ .............................................. A61F 5/00
[52] U.S. Cl. ................. 128/80 C; 128/80 F; 128/80 R; 2/22
[58] Field of Search ............... 128/80 R, 80 C, 80 F; 2/22, 24

[56] References Cited

U.S. PATENT DOCUMENTS

| 2,883,982 | 4/1959 | Rainey | 128/80 F |
|---|---|---|---|
| 4,024,584 | 5/1977 | Smith | 2/22 |
| 4,692,946 | 9/1987 | Jurga | 2/22 |
| 4,751,748 | 6/1988 | Ekins | 128/80 C |
| 4,803,975 | 2/1989 | Meyers | 2/22 |
| 4,854,308 | 8/1989 | Drillio | 128/80 C |
| 4,888,826 | 12/1989 | Parsons et al. | 2/22 |
| 4,890,607 | 1/1990 | Townsend | 128/80 C |

Primary Examiner—Clifford D. Crowder
Assistant Examiner—Ren Yan
Attorney, Agent, or Firm—McCormick, Paulding & Huber

[57] ABSTRACT

A thigh and knee protector includes separate guards hingedly connected coaxially with the knee joint. The thigh guard has a plate that fits into an inside pocket in the garment normally worn outside the protector (such as a pair of football pants). The plate can be selectively positioned on the protector's thigh guard to assure precisely locating the protector's hinge joint structure relative to the actual knee joint.

10 Claims, 7 Drawing Sheets

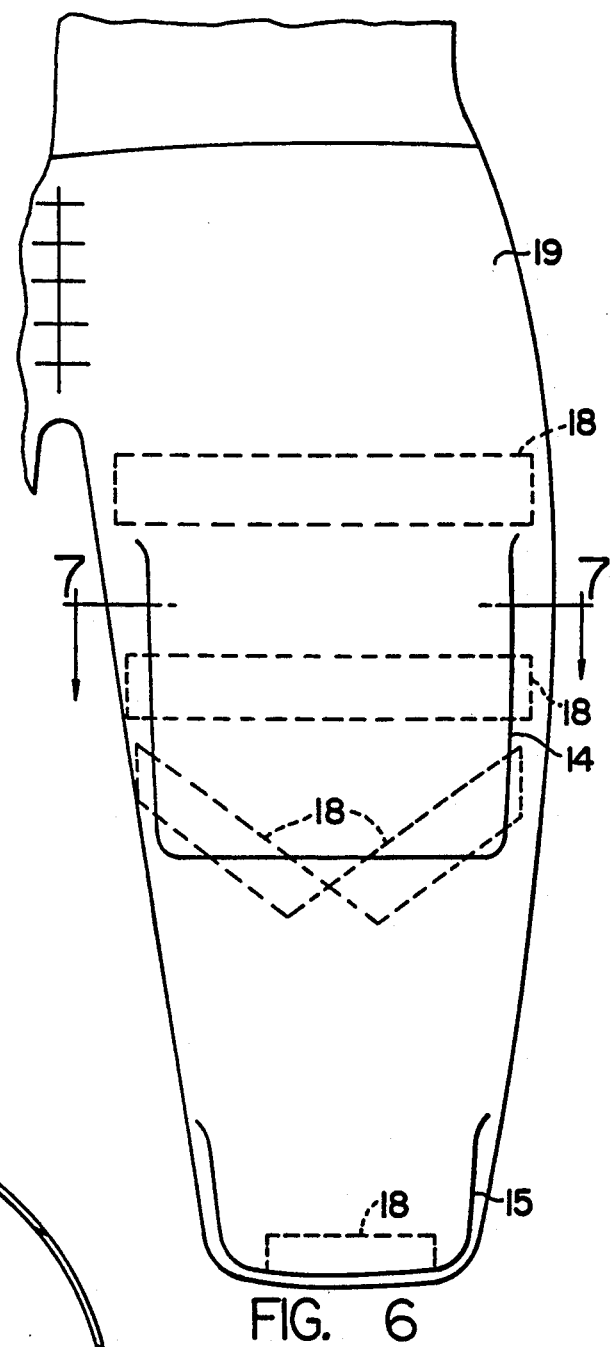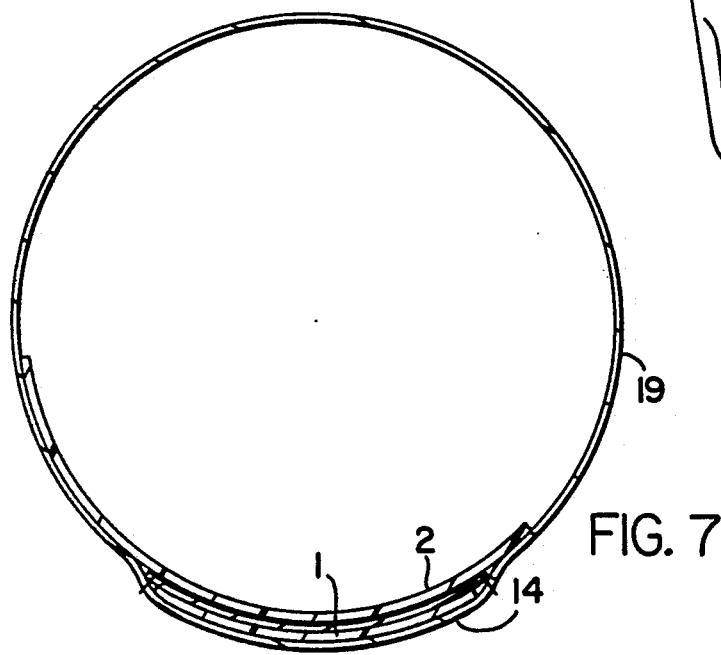

THIGH AND KNEE PROTECTIVE DEVICE

This is a continuation-in-part of co-pending application Ser. No. 203,092, filed on June 7, 1988, now abandoned.

BACKGROUND OF THE INVENTION

Football players and hockey players are particularly susceptible to injury in the area of the knee, and the typical uniforms for such athletes generally provide pockets in the garments themselves for receiving pads or plates to protect the thigh and sometimes the knee area, and in the case of hockey players the shin area as well.

As separate protective devices leg braces of one kind or another have been proposed, and some prior art configurations are dipicted in the following prior art patents:

U.S. Pat. No. 3,945,047 issued in 1974 to Jarrell
U.S. Pat. No. 3,742,517 issued in 1973 to Bednarczuk et al, and
U.S. Pat. No. 2,195,024 issued in 1940 to Bullock.

These prior art knee brace devices are not intended to provide protection for either the thigh or the area below the knee, particularly the shin area, nor are these devices particularly well suited for use with a typical football player or hockey player pants garment of the type equipped with pockets to receive protective pads.

The prior art does include some suggestion of a combination knee protector and thigh and/or shin guard protector U.S. Pat. No. 3,259,910 to Daignault being typical, but here again there is no suggestion of how such a protector can be incorporated with or used in conjunction with present day football player and/or hockey player clothing generally.

SUMMARY OF INVENTION

In accordance with the present invention a thigh and knee protector is disclosed that is particularly well suited for use with conventional football player and/or hockey player garments.

In accordance with the present invention left and right hand protective devices are provided, each with a thigh shell or guard having a portion extending well around the upper part of the leg to protect against injuries from the lateral or outside, which thigh shell is hingedly connected to a knee guard or shell by means of a unique joint that affords a limitation as to the angular deflection for the knee joint itself. The thigh guard or shell includes suitable padding or the like, and in accordance with the present invention a rigid thigh locator plate is provided on the inside of the thigh shell by means associated with the upper marginal edge of the thigh plate. The configuration of the thigh plate is generally trapezoidal so as to be received in the pocket provided in a typical football, hockey player pants leg, or athletic girdle. No other support is provided for the thigh shell or guard other than this plate avoiding the need for strapping and encircling the thigh which straps tend to impede the wearer in his use of the device on the athletic field or on a hockey rink.

The knee shell or guard may include a depending portion to protect the skin particularly where the device is adapted for use by hockey players. This knee shell can be held in place by means similar to that referred to above with reference to the thigh shell or guard, but preferably a strap is provided immediately below the knee joint area to secure this knee shell in place. Where a shin guard protective device is provided a second strap may be provided for around the user's ankle.

The preferred form for the limiting means associated with the knee joint pivot pins joining the thigh shell to the knee shell may take the form of an arcuate slot and associated pin in one and the other of these two components to restrict the angular travel of the knee shell with respect to the thigh shell. Suitable padding is provided for on the inside of both the knee and thigh shells, and in accordance with the present invention the locating thigh plate is provided on the outside of the thigh shell to be received in the pocket normally provided on the inside of the leg portion of a football player's pants, of a hockey player's garment or athletic girdle.

BRIEF DESCRIPTION OF THE DRAWINGS

FIG. 6 is a front view of the left leg of a typical football player's pants showing the inside thigh and knee pad pocket.

FIG. 7 is a sectional view showing the garment of FIG. 6 assembled with the device of FIGS. 1-5. FIG. 7 is taken generally on the line 7—7 of FIGS. 1 and 6.

DETAILED DESCRIPTION OF FIGS. 1-7

Referring first to FIG. 6, a right leg portion of a conventionally configured pair of football pants is illustrated. The inside thigh pocket 14 of the pants 19 is provided in the usual place on both legs (one shown) to receive a conventional thigh pad (not shown). This pocket is utilized to support a device of the present invention. A lower pocket adjacent the front of the knee (provided in some garments of this type) may or may not be utilized for supporting a device of the present invention inside the garment. As illustrated in the device of FIGS. 1–5 two support plates 1 and 6 are provided for insertion in these pockets, 14 and 15 respectively.

Figure 1:
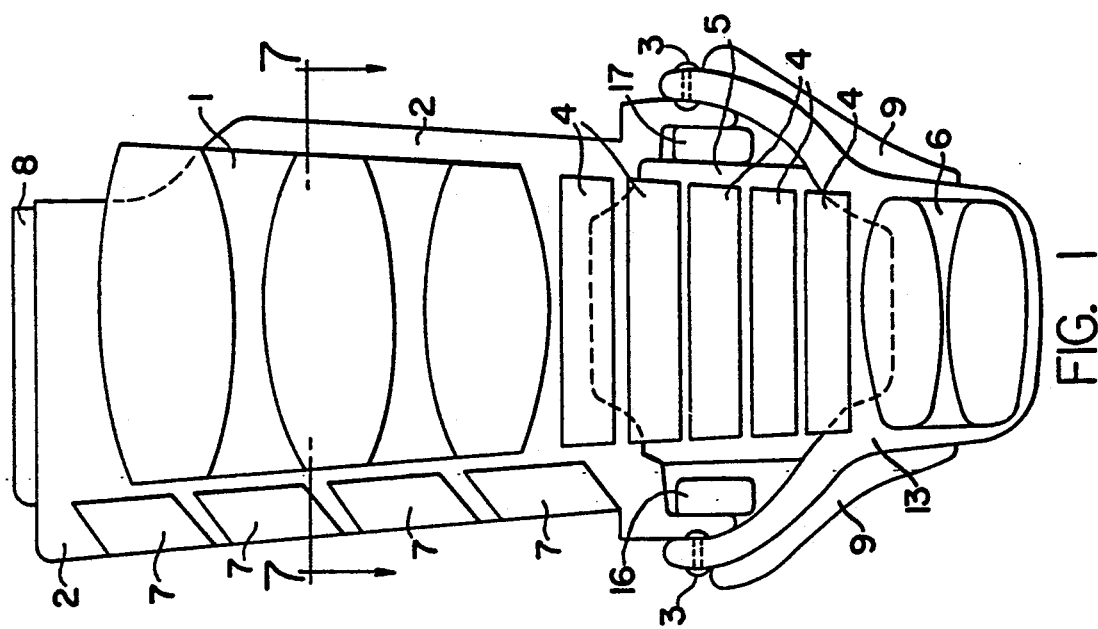
FIG. 1 is a front elevational view showing the plastic thigh shell and plastic knee shell together with the means pivotably connecting them at the knee joint.
Figure 3:
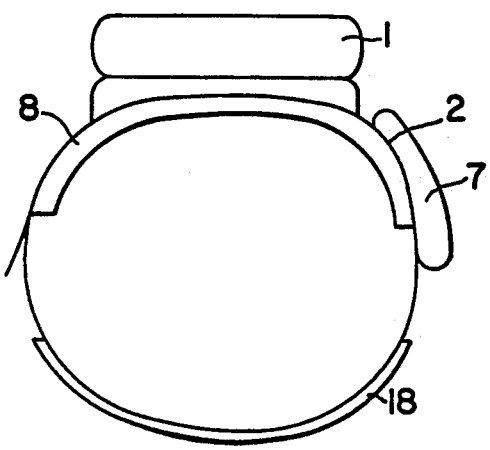
FIG. 3 is a top plan view of the device illustrated in FIGS. 1 and 2.
Figure 4:
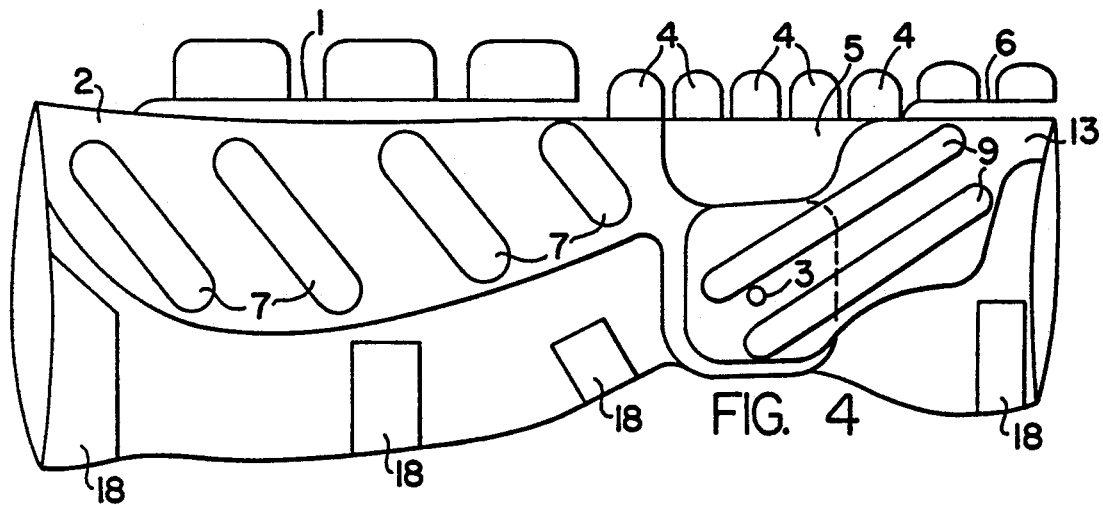
FIG. 4 is a side view with the knee in its extended position.
Figure 5:
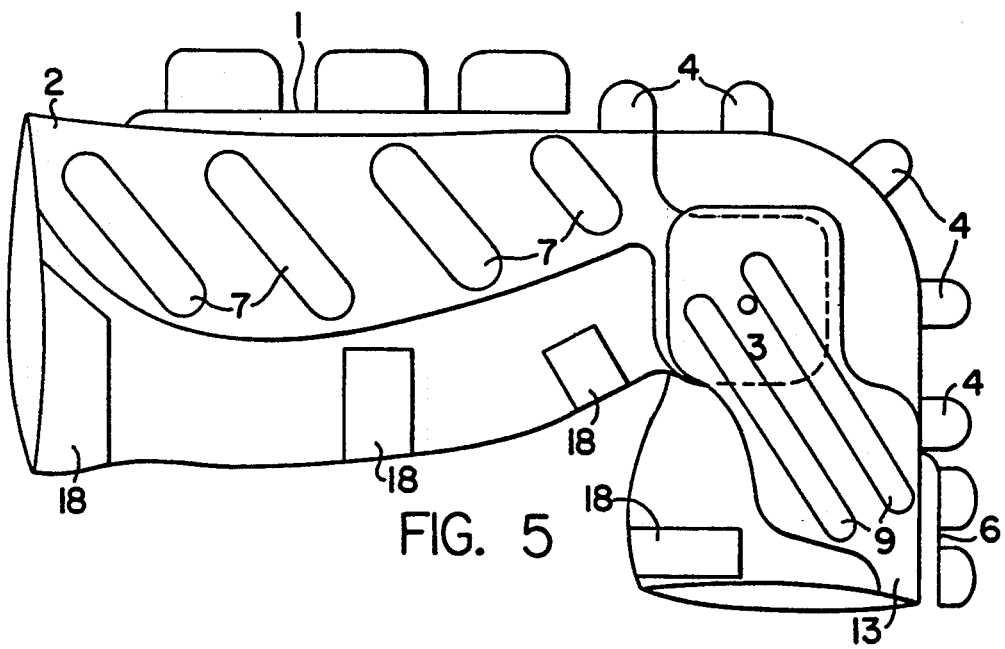
FIG. 5 is a side view with the knee in a 90 degree flexed position relative to that in FIG. 4.

With particular reference to FIG. 1 a stiff or hard plastic thigh shell or guard 2 is shaped to fit the right leg of the wearer. Padded portions indicated generally at 7, 7 extend around the side of the leg to absorb impacts or side loads on the leg. At the front of this thigh shell the thigh plate 1 is provided in spaced relationship to the front of the thigh shell 2 so as to provide a space between the thigh plate 1 and thigh shell or guard 2 as shown in FIGS. 4 and 5. This space is adapted to receive the pocket portion 14 at the inside of the garment as shown in FIG. 7. Velcro straps may be provided on the thigh plate 1 to cooperate with complementary Velcro straps as suggested at 18 on the garment 19. These straps may not be necessary if the thigh plate 1 is provided of suitable shape and with a suitable space between it and the thigh shell 2 so as to snugly fit into the thigh pocket 14 of the pants 19.

Two pivot pins or rivets 3, 3 are provided between the lower end of the thigh shell and the upper end of the knee shell or guard 13 so as to permit at least 90 degrees of motion as suggested in the drawings of FIGS. 4 and 5. I prefer to provide means for limiting this angular motion of the leg and in the device of FIGS. 8–15 I have disclosed a preferred means for protecting the leg against excessive angular motion. Such lower leg motion hyperextension and hyperflexion, common injuries to football players generally when the leg is bent either forwardly too far or rearwardly too far during impact.

Figure 8:
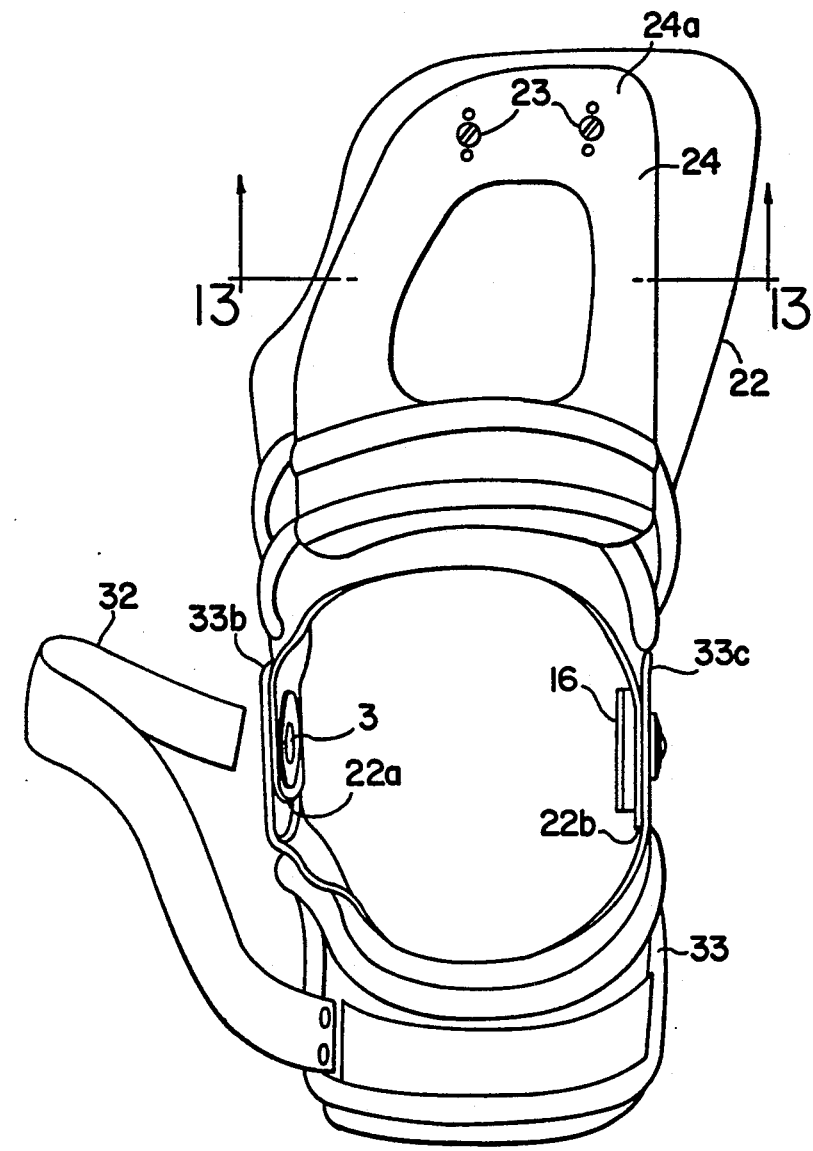
FIG. 8 is a front elevational view of an alternative embodiment for the right leg of the invention without the pad provided therein, and without the garment with which this device is normally used by the user.

Each of the pivot pins or rivets 3 extends through an upper portion of the lower knee guard 13 and a lower portion of the thigh guard 2, which portions overlap one another. In order to protect the user's knee area these rivets are covered by pads of relatively soft foam material provided as suggested generally at 16 (FIG. 8).

Figure 10:
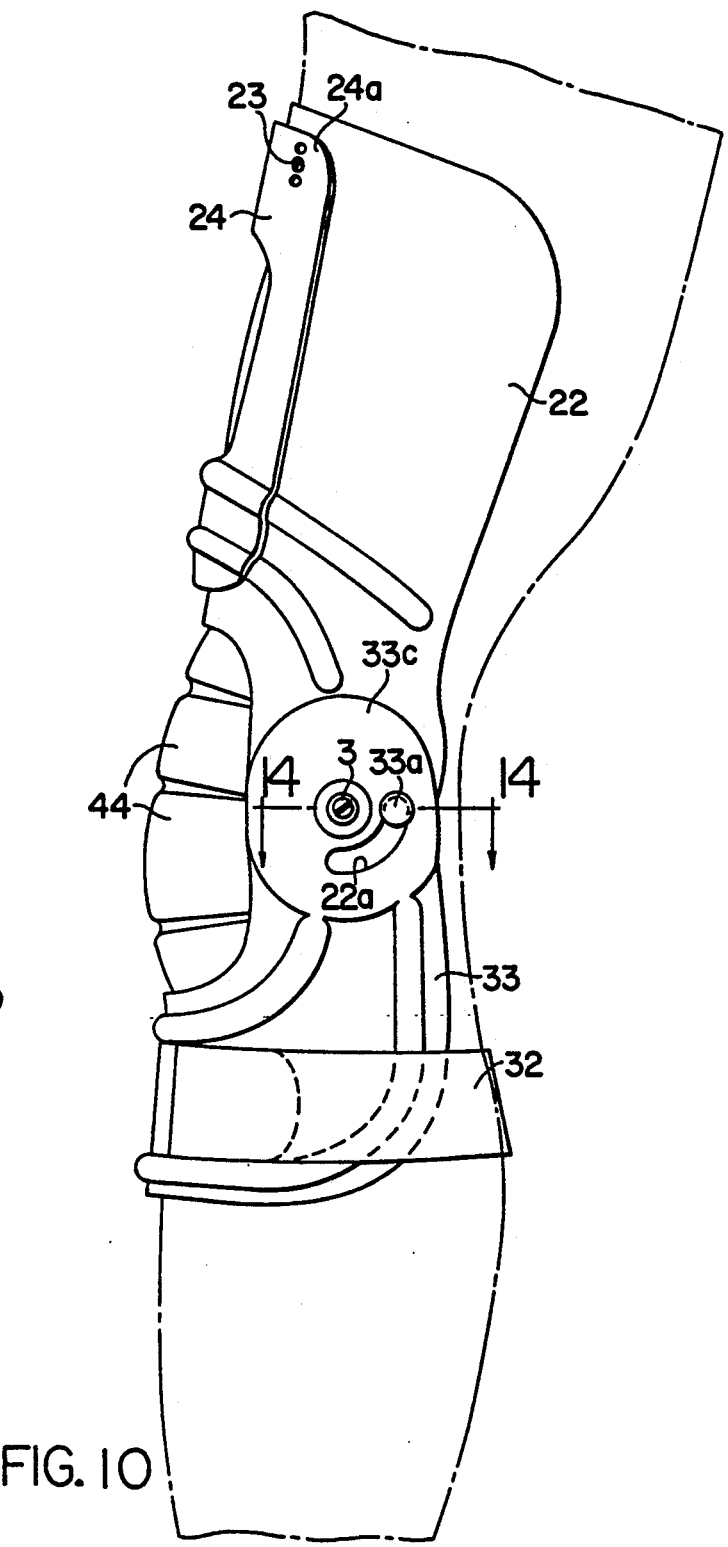
FIG. 10 is a right side elevational view of the device of FIGS. 8 and 9 with the pad provided therein, and with the user's leg shown also.
Figure 12:
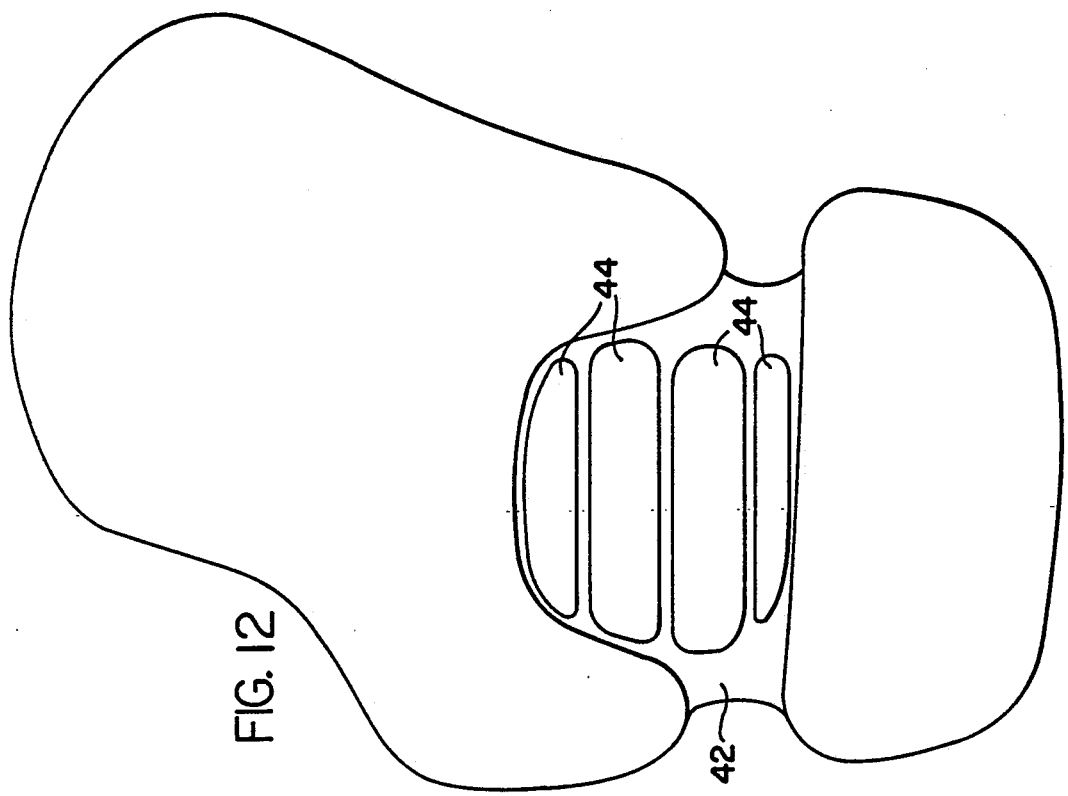
FIG. 12 is a front elevational view of the pad provided inside the device of FIGS. 8, 9 and 11, the pad having a flat configuration in this view, but adapted to conform to the shape of the inside of the FIG. 11 device as suggested in FIG. 10.
Figure 11:
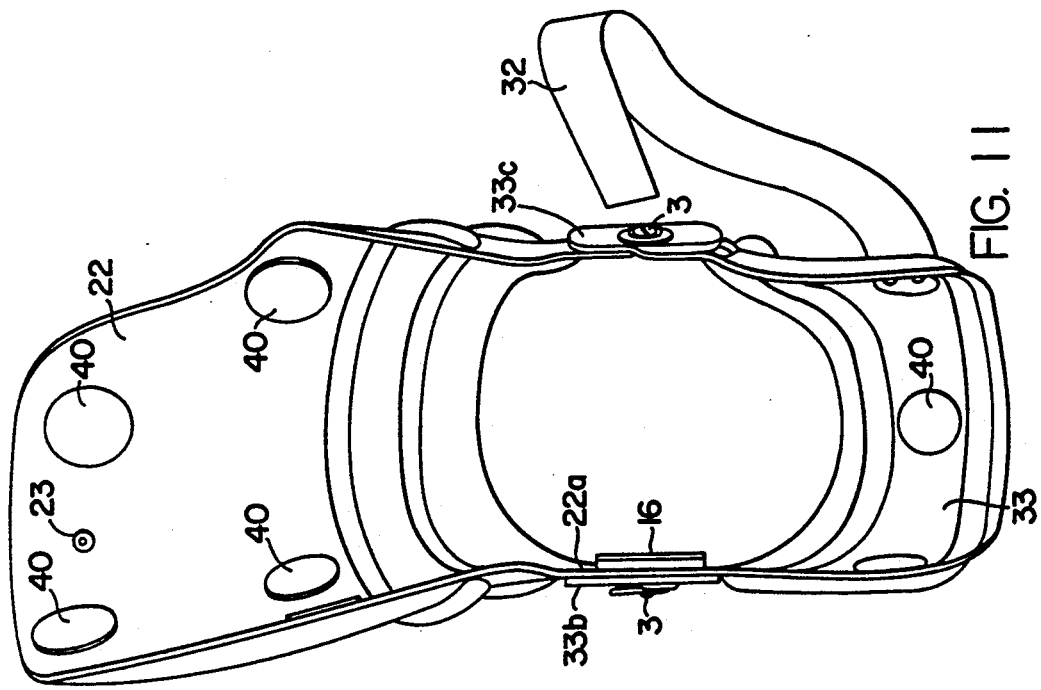
FIG. 11 is a rear elevational view of the device illustrated in FIGS. 8 and 9.
Figure 15:
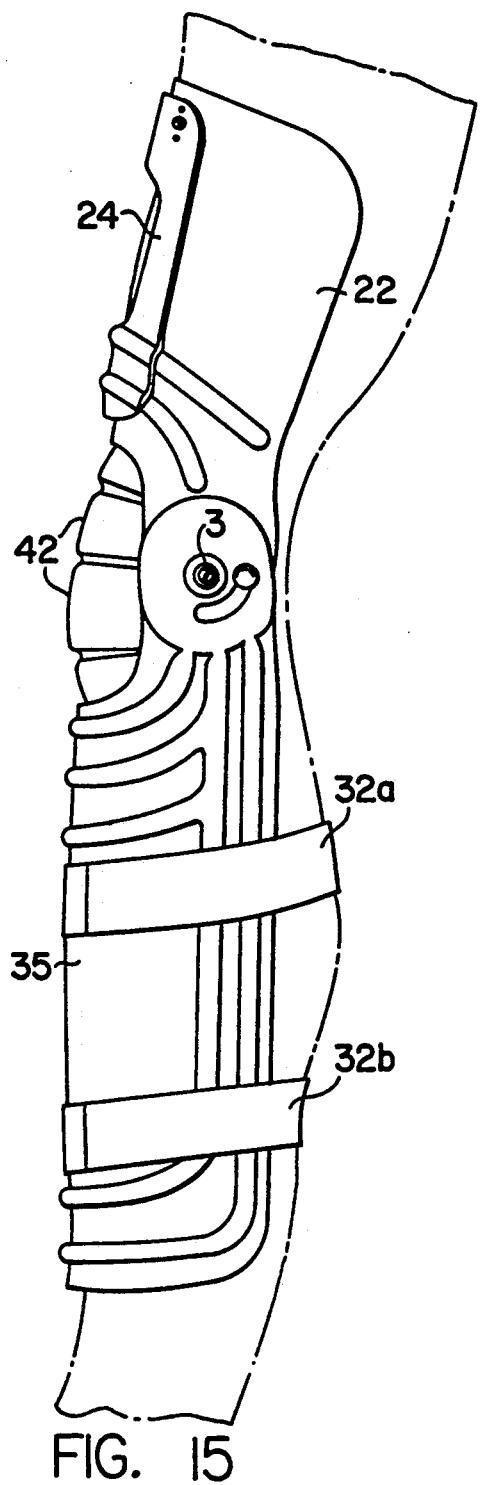
FIG. 15 is a right side elevational view of a device similar to that shown in FIGS. 1-14 but instead of the short lower knee shell this device includes a longer shell to protect the users shin area.

Turning now to FIG. 10, the means for achieving limited angular movement of the thigh and knee guards 22 and 33 relative to one another is accomplished by providing an arcuate groove 22a in one of these components, and providing a pin 33a in the other components so as to afford a convenient means for limiting the angular rotation of the thigh guard 22 relative to the knee guard 33. Although FIG. 10 illustrates the pin and slot configuration in an alternative embodiment of the present invention it will be apparent that the version of FIGS. 1–8 can be provided with this feature.

Figure 2:
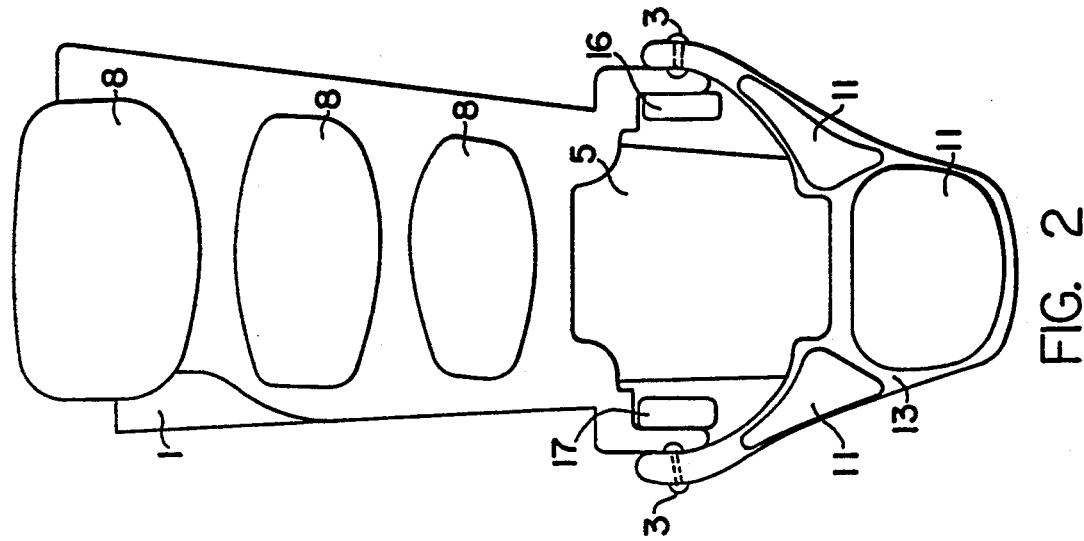
FIG. 2 is a rear view of the FIG. 1 assembly.

The hard shell thigh and knee guards or shells are fitted on the inside with Velcro material that is adapted to receive and to locate either a one-piece pad configuration as illustrated in the embodiment of FIGS. 8–14 or to receive individual pads as best shown at 8, 8 in FIG. 2 with respect to the embodiment of FIGS. 1–7. FIG. 2 shows the inside of the thigh guard or plate 2 and the pads 8, 8. In the area of the knee itself a flexible accordion type pad is provided with segments 4, 4 joined together by elastic cloth member 5 to permit expansion and contraction of this particular pad due to the flexure requirements at the knee joint. Finally, pads 11, 11 are provided in the knee guard itself in this embodiment. However, it will be recognized that a single larger pad can be provided inside the pivotably connected thigh and knee guards, and held in place by strategically placed Velcro strips as discussed hereinbelow with particular reference to FIGS. 8–14.

In the embodiment of FIGS. 1–7 lateral side pads 7, 7 are attached to the lateral side of the thigh guard 2 and the knee guard or shell 13 also has lateral pads 9, 9 to provide a padding between the hard shell and the user's leg. The elastic cloth 5 is preferably attached to the thigh shell 2 and the knee guard 13, and this cloth may be of annular configuration to surround the knee joint area of the user. Condyle pad 16 and 17 may be provided on the inside of both rivet connections or may be provided only at the outside of both leg protective devices as described hereinafter with reference to FIGS. 8–14.

FIG. 7 illustrates the pants leg 19 of the football garment shown in FIG. 6 with the thigh shell 2 inside the pants leg and with the associated thigh plate 1 inside the pocket 14 of the pants 19. As so constructed and arranged the plate 1 provided inside the pocket 14 of the garment 19 supports and locates the thigh guard and thereby supports and locates the entire assembly on the user's leg. If desired and as shown in the embodiment of FIGS. 1–7, a knee plate 6 may be provided in a knee pocket 15 provided in the garment 19. The thigh plate 1 and knee plate 6 are of a suitable size and shape so as to be received in these pockets for supporting and locating the device of FIGS. 1–7.

DETAILED DESCRIPTION OF FIGS. 8–14

Figure 13:
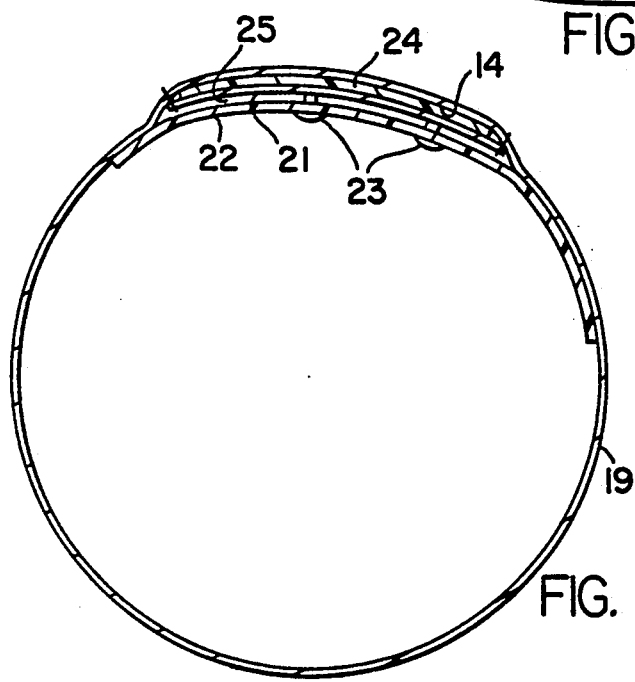
FIG. 13 is a sectional view taken on the line 13—13 of FIG. 8.
Figure 14:
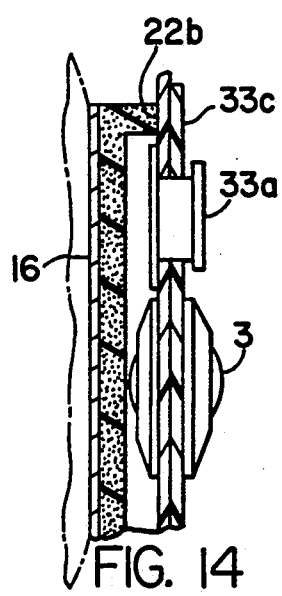
FIG. 14 is a sectional view taken on the line 14—14 of FIG. 10.

FIGS. 8–14 illustrate an alternative embodiment wherein the thigh shell or guard 22 is held in place by a thigh plate 24 secured to the front of the thigh guard 22. As shown in FIG. 13 the plate 24 is secured to the thigh guard 22 by two fasteners 23, 23 and a spacer 21 that define a space 25 to receive the interior pocket 14 defined in the leg of the garment 19. The space 25 is provided between the plate 24 and the front of the thigh guard 22 by the spacer 21. The plate 24 is preferably joined to the thigh guard along the upper marginal edge 24a of the plate 24 by adjustable means. Several sets of holes are provided in the plate 24 as best shown in FIG. 8. This construction allowed the screws 23, 23 to secure the plate and the spacer block of resilient plastic to the thigh guard 22 at a predetermined position. The spacer block comprises a resilient material to cushion impact forces between the thigh guard 22 and plate 24.

Figure 9:
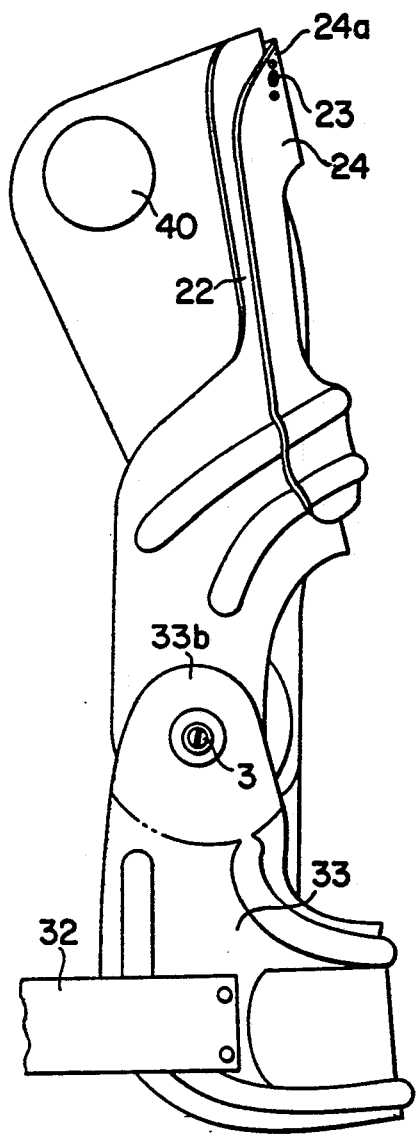
Fig. 9 is a left side elevational view of the device illustrated in FIG. 8.

The embodiment of FIGS. 8–14 is similar to that of FIGS. 1–7 inclusively in that a lower knee guard 33 is pivotably connected to the thigh guard 22 by means of aligned rivets of the type referred to previously and indicated generally at 3, 3 in FIGS. 8, 9 and 10. A pin 33a provided in the knee guard 33 limits relative pivotal movement of the knee guard 33 relative to the thigh guard 22 as a result of being received in an arcuate slot 22a provided for this purpose in radially spaced relationship to the pivot pin or rivet 3. The knee guard 33 is held in place by a strap 32 which wraps around behind the calf of the wearer's leg as suggested in FIG. 10. Velcro material is provided for securing the strap in place, and this strap obviates the need for a knee plate to hold the knee guard 33 in place such as described previously with reference to FIG. 4 and as shown at 6 in FIG. 4. The strap 32 also obviates the need for providing a garment pocket such as indicated generally at 15 in FIG. 6 to receive such a plate. Such a strap 32 can conveniently be worn about the lower portion of the leg as shown in FIG. 10 whereas providing such a strap around the upper or thigh portion of the leg is not acceptable because of the necessity for the back of the user's thigh to be free of such constraints in the environment of an athletic contest of the type for which the present device has been designed. This allows complete mobility of the leg and of the knee joint.

Thus, the adjustably mounted thigh guard support plate 24 providing support for the device as described is an essential element of the present invention and can be found in all versions of the invention as disclosed herein.

As so constructed the thigh and knee guards 22 and 33 are pivotably connected to one another on an axis defined by the rivets 3, 3. The lower portion of thigh guard is of inverted U-shape, the legs 22a and 22b of the U being adapted for placement alongside the wearer's knee joint. In the left leg version shown (the right leg version being a mirror image thereof) only the outside rivet has a pad 16. No pad is provided on the inside rivet to allow both legs to move more freely past one another during the wearer's leg movements.

The lower leg guard, or knee guard 33 has upstanding projections 33b and 33c which are arranged adjacent to said U-shaped legs 22a and 22b of the thigh guard 22 and pivotably joined on the above mentioned common axis of rivets 3 and 3.

These U-shaped portions also define a knee opening (best shown in FIGS. 8 and 9) that assures freedom of movement for the wearer's knee. A one piece pad (FIG. 12) is shaped to fit inside the thigh and knee guards as suggested in FIG. 10. Velcro elements 40, 40 are provided on the interior of these guards 22 and 33 and cooperate with the pad material itself to removably secure the pad in place. The pad is fabricated from a suitably resilient foam material, and the medial portion 42 is preferably formed with horizontally extending ribs 44, 44 to provide stiffness for protection of the kneecap but yet allow for flexing of the knee joint during the wearer's leg movements.

As shown in FIG. 13 the thigh guard 22 has an arcuate shape that fits the wearer's thigh and the pad (not shown) fits between the thigh and this thigh guard 22. The screw fasteners 23, 23 support the plate 24 in spaced relation to the thigh guard 22 so that the pocket 14 of the garment 19 will receive this plate and support the device in the proper place. Strap 32 also aids in such placement on the wearer's leg but the chief support comes from the plate 24 in the pocket 14 of the wearer's garment 19.

DETAILED DESCRIPTION OF FIG. 15

In this view the knee guard of FIGS. 8–14 is replaced by a shin guard 35 that is pivotably supported from the thigh guard 22 in the same manner as described previously. Two straps 32a and 32b are provided on the shin guard 35 to encircle the wearer's lower leg as shown. The pad has a medial portion 42 like that described above with reference to FIG. 12, and has a lower portion that insulates the wearer's lower leg from impacts sustained by the stiff plastic shin guard 35.

I claim:

1. In combination with an article of athletic apparel of the type having at least one portion that encircles the wearer's thigh and that defines an inside pocket with an upwardly open entry to the pocket, a thigh and knee guard for use between the wearer's leg and the pocket defining article of apparel, said thigh and knee guard comprising:

(a) a molded plastic thigh guard having an upper portion of arcuate cross section conforming to the user's thigh and a lower portion of inverted U-shaped with inside and outside extensions adapted for placement alongside the inside and outside of the wearer's knee, (b) a lower leg guard having an upper portion of U-shape with inside and outside projections adapted for placement alongside said inside and outside extensions respectively, (c) means pivotably connecting said thigh guard extensions and said lower leg guard projections to provide limited pivotal movement of said lower leg guard relative to said thigh guard, (d) pad means removably secured to said thigh and lower leg guards and including a medial portion for covering the wearer's kenn, said thigh and lower leg guards defining a knee opening for said medial portion, (e) a plate secured to said upper portion of said thigh guard and extending downwardly in spaced relationship to said thigh guard upper portion, said plate shaped to fit into said apparel article pocket for supporting and locating said thigh guard and lower leg guard on the wearer's leg and inside said apparel article.

2. In combination with claim 1, said thigh guard extensions in said lower leg guard projections having openings therein, said pivotal means connecting said thigh guard extensions to said lower leg guard projections comprises rivets in said openings, and pin and slot means provided in said thigh guard extensions and said lower leg guard projections for limiting the pivotal movement thereof to prevent hyperextension and hyperflexion.

3. In combination with claim 1 means supporting said plate in one of several selected positions to permit more precise positioning of the thigh guard and hence of the pivot axis movement for said thigh and lower leg guards relative to the pocket and the knee joint of the wearer.

4. In combination with claim 1 said plastic thigh guard and lower leg guard is fabricated from a high impact plastic such as ABS or the equivalent.

5. In combination with claim 1 VELCRO hook and loop fastener means for securing said pad means to said thigh guard.

6. In combination with claim 2 means supporting said plate in one of several selected positions to permit more precise positioning of the thigh guard and hence of the pivot axis movement for said thigh an lower leg guard relative to the pocket and the knee joint of the wearer.

7. In combination with claim 4 means supporting said plate in one of several selected positions to permit more precise positioning of the thigh guard and hence of the pivot axis movement for said thigh and lower knee guard relative to the pocket and the knee joint of the wearer.

8. In combination with claim 7 including VELCRO hook and loop fastener means for securing said pad means to said thigh guard.

9. In combination with claim 8 said means supporting said plate having several equal openings in said plate and screw fasteners provided in selected openings.

10. In combination with claim 9 said means supporting said plate further including a resilient spacer between said plate and thigh guard.

* * * * *